United States Patent [19]
Rahman et al.

[11] Patent Number: 5,665,710
[45] Date of Patent: Sep. 9, 1997

[54] METHOD OF MAKING LIPOSOMAL OLIGODEOXYNUCLEOTIDE COMPOSITIONS

[75] Inventors: Aquilur Rahman, Gaithersburg, Md.;
Alain Thierry, Washington, D.C.;
Anatoly Dritschilo, Bethesda, Md.

[73] Assignee: Georgetown University, Washington, D.C.

[21] Appl. No.: 165,000

[22] Filed: Dec. 10, 1993

Related U.S. Application Data

[63] Continuation of Ser. No. 28,593, Mar. 8, 1993, abandoned, which is a continuation of Ser. No. 516,988, Apr. 30, 1990, abandoned.

[51] Int. Cl.$^6$ ............................. C07H 1/00; C07H 21/00
[52] U.S. Cl. ..................... 514/44; 424/450; 536/23.1; 536/24.1; 435/172.1
[58] Field of Search .................. 424/450; 536/24.1, 536/23.1; 514/44; 435/172

[56] References Cited

U.S. PATENT DOCUMENTS

| | | | |
|---|---|---|---|
| 4,201,767 | 5/1980 | Fullerton | 424/89 |
| 4,210,746 | 7/1980 | Kerr et al. | 536/24.1 |
| 4,235,871 | 11/1980 | Papahadjopoulos | 424/450 |
| 4,235,877 | 11/1980 | Fullerton | 424/89 |
| 4,241,046 | 12/1980 | Papahadjopoulos | 424/450 |
| 4,261,975 | 4/1981 | Fullerton | 424/89 |
| 4,394,448 | 7/1983 | Szoka, Jr. | 424/172 |
| 4,663,161 | 5/1987 | Monnino et al. | 424/89 |
| 4,861,588 | 8/1989 | Neurath et al. | 424/406 |
| 4,871,488 | 10/1989 | Monnino et al. | 424/89 |
| 4,904,582 | 2/1990 | Tullis | 435/6 |
| 5,279,833 | 1/1994 | Rose | 424/450 |

FOREIGN PATENT DOCUMENTS

| | | |
|---|---|---|
| 61-137471 | 6/1986 | Japan . |
| 62-157468 | 7/1987 | Japan . |
| 2267592 | 11/1990 | Japan . |
| 3259193 | 11/1991 | Japan . |

*Primary Examiner*—James O. Wilson
*Attorney, Agent, or Firm*—Foley & Lardner

[57] ABSTRACT

A liposome, which contains an oligodeoxynucleotide or an analog thereof.

3 Claims, 3 Drawing Sheets

METHOD OF MAKING LIPOSOMAL OLIGODEOXYNUCLEOTIDE COMPOSITIONS

This application is a continuation of application Ser. No. 08/028,593, filed Mar. 8, 1993, which is a continuation of Ser. No. 07/516,988, filed Apr. 30, 1990, both now abandoned.

BACKGROUND OF THE INVENTION

1. Field of the Invention

The present invention relates to liposomal oligodeoxynucleotides and a method of using the same in cancer therapeutics.

2. Description of the Background

Although a variety of anticancer drugs are presently used against the many forms of cancer, one of the major limitations of cancer chemotherapy is the lack of specificity of anticancer drugs for malignant cells. Due to this lack of specificity, existing anticancer drugs are distributed indiscriminately throughout the body when used, posing treatment-limiting toxicities.

Many of the drugs used in chemotherapy are natural products or derivatives thereof which either block enzyme pathways or randomly interact with deoxyribonucleic acid (DNA). Others are cytotoxic in nature, which function by exploiting quantitative biochemical and kinetic differences between malignant and normal cells.

Similarly, antiviral agents which are designed to target viral-specific processes unique to infected cells, often cause an array of nonspecific toxic effects that limit their use.

Thus, a need clearly continues to exist for cancer chemotherapeutical agents which exhibit a high degree of discrimination between malignant and normal cells, and which cause a minimum, if any, of nonspecific toxic side effects. A need also continues to exist for antiviral agents which can target viral-specific processes unique to infected cells without causing an array of toxic side effects.

SUMMARY OF THE INVENTION

In accordance with the present invention, a liposomally encapsulated oligonucleotide is provided which exhibits a high degree of specificity for cancerous cells and/or viruses.

The present invention also provides a method of preparing liposome encapsulated oligonucleotides referred to inter alia as the minimal volume entrapment method.

The present invention also provides a method of treating cancerous cells and/or viruses.

The above objects and others which will be described, are provided, in part, by a liposome, which contains an oligonucleotide or an analog thereof.

DETAILED DESCRIPTION OF THE PREFERRED EMBODIMENTS

Figure 1:
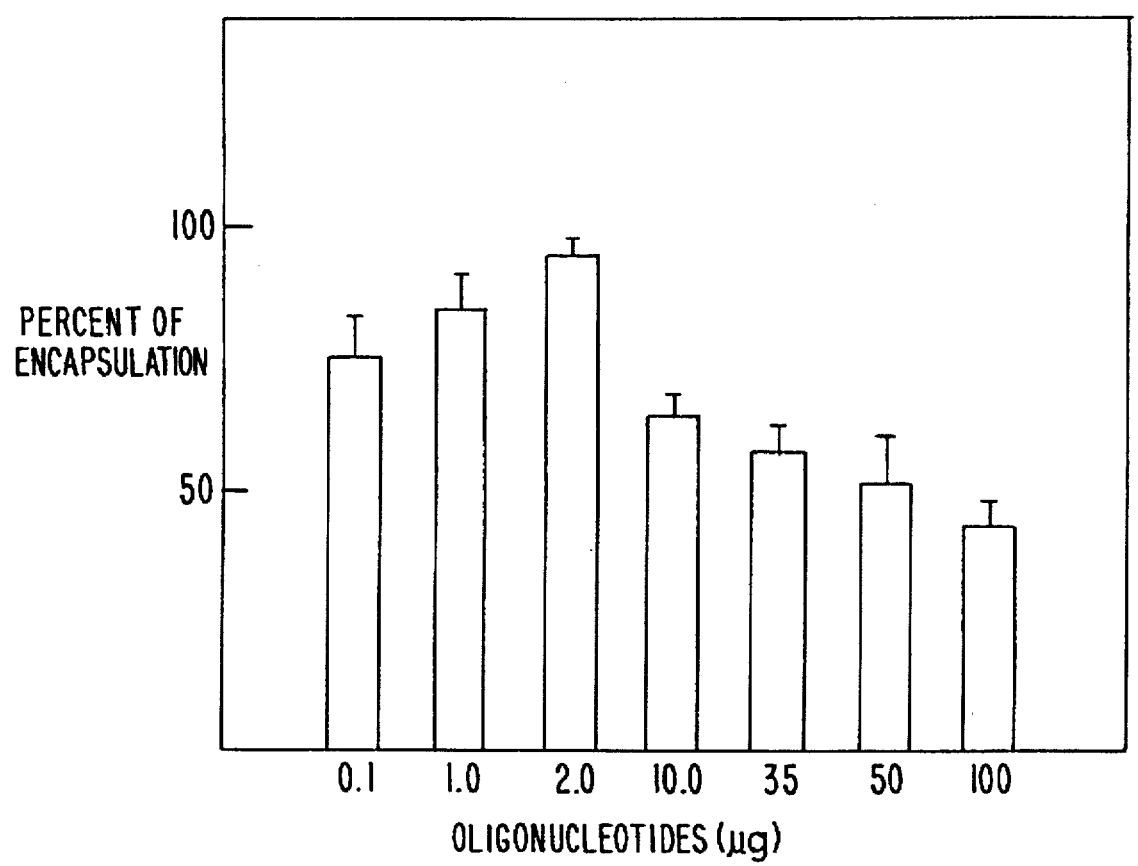
FIG. 1 illustrates the encapsulation efficiency of oligodeoxynucleotides in liposomes as a function of concentration.

In accordance with the present invention, methods of effecting cancer chemotherapy and antiviral therapy are provided by using mammalian, preferably human, messenger RNA (mRNA) as the primary drug target. In, perhaps, the broadest form, the present invention entails the use of an oligonucleotide to hybridize with an exogenous target sequence of mRNA or DNA in order to prevent the expression of the target mRNA or DNA encoded protein product. This process is referred to as "translation arrest" or "transcription arrest". Since the mRNA sequence expressed by the gene, for example, is called the "sense base sequence" the complimentary sequence is the "antisense sequence". Based upon elementary principals of molecular biology, it is presumed that the oligonucleotide molecule hybridizes with the target mRNA molecule by hydrogen-bonded base pairing. Due to the many recent advances in molecular biology and synthetic chemistry, it is now possible to obtain short, synthetic oligodeoxynucleotides which can be used as potential therapeutic agents. In fact, in accordance with the present invention, these short, synthetic oligodeoxynucleotides can be used to bind to either mRNA sequences or target DNA sequences in order to selectively block translation or transcription, respectively, of a particular gene.

Prior to the present invention, the use of oligodeoxynucleotides as therapeutic agents was extremely limited due to their instability in biological environments. In particular, deoxynucleotides contain a phosphodiester bond which is readily cleaved by many deoxyribonuclease enzymes which are present in the cells. While exonucleases cleave from the end of a DNA chain, endonucleases cleave anywhere along the chain. In fact, the half-life of oligodeoxynucleotides in the cellular environment has been estimated to be anywhere from a few minutes to a few hours due to rapid enzymatic degradation. See Holt J. T. et al, *Mol. Cell. Biol.* 8:963–973 (1988). This rapid enzymatic degradation is particularly debilitating to any method which depends upon the sequence or length of a chain molecule as a single cleavage could render the oligodeoxynucleotide useless. Additionally, oligodeoxynucleotide degradation may give rise to various mononucleotides which could cause host toxicity. Further, the rapid enzymatic degradation mentioned above may be problematic in that the same may take place before hybridization can occur between the oligonucleotide and a target mRNA or DNA sequence.

Quite surprisingly, in accordance with the present invention, it has now been discovered that: 1) liposomally encapsulated oligodeoxynucleotides can penetrate into cells, 2) the oligodeoxynucleotides are stable in the cellular environment, and 3) the oligodeoxynucleotides hybridize effectively with the target sense mRNA or DNA sequences of interest once inside the cell membrane.

Thus, in accordance with the present invention is provided a liposome, which contains an oligonucleotide or analog thereof enclosed therein.

The oligodeoxynucleotides of the present invention are, by definition, single-stranded deoxynucleotide sequences which can range in length from about 3 to 500 mer. Preferably, however, the sequence is from about 4 to 100 mer. More preferably, however, the sequence is from 4 to 50 mer, with sequences of from 4 to 30 mer being the most preferred sequences. Most preferred, however, are sequences from about 4 to 20 mer. However, sequences which are shorter or longer than the above sequences may be used as needed.

The oligodeoxynucleotides used may be prepared by solid state synthesis or even using recombinant DNA techniques. Also, a desired oligonucleotide may be custom ordered from any number of custom synthesis companies which are well known to those skilled in the art. In fact, methods for synthesizing oligonucleotide sequences are quite well known.

Also provided are methods for treating cancerous cells and/or viruses, whereby the translation of one or more sense mRNA sequences or the transcription of DNA sequences contained therein are arrested. This effect results in a highly specific cytotoxicity for cancerous cells and is highly effective in targeting viral-specific processes.

In one aspect of the present invention, it has been discovered that the present liposome encapsulated oligodeoxynucleotides are highly stable in vitro. The present liposome encapsulated oligodeoxynucleotides can be stored at 4° C. in excess of one week, for example.

In another aspect of the present invention, it has been discovered that the present liposome encapsulated oligodeoxynucleotides are highly effective in penetrating cellular membranes. For example, at a given concentration of free oligodeoxynucleotides and liposome encapsulated oligodeoxynucleotides, the liposome encapsulated oligodeoxynucleotides are generally delivered to cells in amounts of up to 30 times greater than the amount delivered using free oligodeoxynucleotides.

In yet another aspect of the present invention, it has been discovered that the present liposome encapsulated oligodeoxynucleotides are highly stable in the cellular medium. For example, the present inventors have found that intact oligodeoxynucleotides are present in the cellular medium during incubation for at least 4 hours. This stability offers sufficient time for hybridization to occur with sense mRNA or DNA sequences.

In still another aspect of the present invention, it has been discovered that the present liposome encapsulated oligodeoxynucleotides exhibit a highly specific cytotoxicity against malignant cells. For example, the present encapsulated oligodeoxynucleotides exhibit a cytotoxicity of 90% or more against many types of cancerous cells. By contrast, free oligodeoxynucleotides exhibit a cytotoxicity of 30% or less against the same malignant cells.

In accordance with the present invention, a variety of lipids may be used to encapsulate the oligodeoxynucleotides in liposomes. Vesicle or liposome wall forming compounds are generally well known as are the methods of their preparation. For example, any number of phospholipids or lipid compounds may be used to form the liposome walls. Representative of such wall forming compounds are: phosphatidylcholine, both naturally occurring and synthetically prepared, phosphatidic acid, lysophosphatidylcholine, phosphatidylserine, phosphatidylethanolamine, sphingolipids, phosphatidylglycerol, spingomyelin, cardiolipin, glycolipids, gangliosides, and cerebrosides, which may be used either singularly or intermixed, such as in soybean phospholipids. Additionally, other lipids such as steroids, cholesterol, aliphatic amines such as long chain aliphatic amines and carboxylic acids, long chain sulfates and phosphates, diacetyl phosphates, butylated hydroxy toluene, tocopherol, retinol and isoprenoid compounds may be intermixed with the phospholipid components to confer certain desired and known properties on the formed liposomes.

Further, synthetic phospholipids containing either altered aliphatic portions such as hydroxyl group, branched carbon chains, cyclo derivatives, aromatic derivatives, ethers, amides, polyunsaturated derivatives, halogenated derivatives or altered hydrophilic portions containing carbohydrate, glycol, phosphate, phosphamide, quaternary amine, sulfate, sulfonyl, carboxy, amine, sulfhydryl, amidizole groups and combinations of such groups can be either substituted or intermixed with the above mentioned phospholipids and used in present invention. Generally, however, such known well forming compounds and methods of use and preparation are described in U.S. Pat. Nos. 4,201,767; 4,235,877; 4,241,046; 4,261,975 and 4,394,448 all of which are incorporated herein in the entirety.

The oligodeoxynucleotides which may be incorporated in liposomes, in accordance with the present invention, may correspond to and be hybridizable with a variety of targets, such as oncogenes, cancer cells, enzymes of proliferative importance to cancer cells, as well as various viruses such as the human immunodeficiency virus (HIV). The oligodeoxynucleotides may be either those which are naturally obtained, cloned or synthesized. For example, two types of antisense oligodeoxynucleotides which may be used are the 18 mer sequence which represents the antisense for the 5'-end of the RAF oncogene, and the 15 mer oligodeoxynucleotide sequence for poly (ADP-ribose) polymerase.

With respect to the first sequence mentioned above, the cDNA of antisense RAF has been cloned and transfected into SQ-20B cells of human head and neck cancer and has been shown to inhibit the tumorigenic activity of SQ-20B cells. See Kasid U., *Science* 243:1354–1356 (1989). Additionally, when these SQ-20B cells are transfected with an anti RAF cDNA vector, they exhibit greater sensitivity to radiation killing than the non-transfected SQ-20B cells.

The second antisense oligodeoxynucleotide sequence mentioned above (15 mer) is important as poly (ADP-ribose) polymerase is known to be important for radiation-induced and drug-induced DNA damage repair in cancer cells. Moreover, it is known that chemical inhibitors of the enzyme poly(ADP-ribose) polymerase promote radiation sensitization. See Thraves P., Radiation Research 104:119–127 (1986). The liposomal carrier system of the present invention for encapsulating the oligodeoxynucleotides is able to overcome the above-mentioned disadvantages which have restricted the use of free oligodeoxynucleotides in therapy. The system of the present invention enhances both the in vitro and the in vivo stability of the oligodeoxynucleotides. As noted above, the present liposomally encapsulated oligodeoxynucleotides are transported into cells in a much higher concentration as compared to what has been observed with free oligodeoxynucleotides. Additionally, the present encapsulated oligodeoxynucleotides demonstrate enhanced biological activity as compared to the free oligodeoxynucleotides. Thus, the amount of oligodeoxynucleotides necessary to perform a specific biological effect is now greatly reduced.

The oligonucleotides which are to be encapsulated are selected to hybridize with either an mRNA or DNA target. The target may be any number of gene types. For example, enzyme genes, multidrug resistance genes (mdr), oncogenes or HIV genes may be targeted. In fact, any gene for which even a partial sequence is known may be targeted.

For purposes of obtaining hybridization, the oligodeoxynucleotide sequence used may correspond with a beginning, middle or end section of the target gene. Further, the oligonucleotide sequence of interest may be used by itself or as the beginning, middle or end of a large sequence whose additional sequences do not interfere with hybridization with the target gene. However, the hybridizing oligonucleotide sequences themselves are of a length as described above.

Inasmuch as the oligodeoxynucleotides are water-soluble, it is expected that a small portion would be entrapped in the aqueous volume of the liposomes. However, this small amount of entrapped oligonucleotide is generally not feasible for practical use. A technique is also provided by the present invention to enhance the encapsulation of the oligodeoxynucleotides. This technique is referred to as the "minimal volume entrapment technique". This technique will now be generally explained.

The use of the minimal volume entrapment technique of the present invention is important as it assures that a high concentration of oligonucleotide will be entrapped in the aqueous liposome layer. Without using this technique, an unacceptably large amount of oligonucleotide will be unentrapped in the liposome layer.

In preparing the liposomes containing the entrapped oligodeoxynucleotides of the present invention, any combination and ratios of lipids may be utilized, however, by varying the lipids used and the ratios thereof, variation in the oligodeoxynucleotide entrapment will clear. For example, the following table is noted:

TABLE 1

Encapsulation Efficiency of Oligodeoxynucleotides in Liposomes as a Function of Lipid Composition

| Lipids | Molar Ratio | Encapsulation Rate |
|---|---|---|
| PC/Ch | 10:6.8 | 11% |
| CL/PC/Ch | 2:10:6.8 | 52% |
| CL/Ch | 7.2 | 54% |
|  | 7:4.5 | 58% |
|  | 10:6.8 | 66% |
| CL/DMPG/Ch | 2:10:6.8 | 60% |
| DMPC/Ch | 10:5 | 17% |
| DMPC/PS/Ch | 10:2:6.8 | 10% |

PC, phosphatidylcholine; Ch, cholesterol; CL, cardiolipin; DMPG, di-myristoyl-phosphatidyl glycerol; DMPC, di-myristoyl-phosphatidyl choline; PS, phosphatidylserine Generally, the various lipids to be used are mixed thoroughly and dried by evaporation under vacuum. To the lipid mixture, a small portion of a solution containing oligodeoxynucleotides is added, such 1-3 µl per mg of lipid. The mixture is then left overnight for incubation following which phosphate buffered saline (PBS) is added to the hydrated film and vigorously vortexed. The mixture is then further hydrated followed by the addition of more PBS. The liposomes are then sonicated and then left for an additional period of time. The only unentrapped oligodeoxynucleotides are separated by centrifugation, and the pellet is rinsed with fresh PBS, centrifuged again, the supernatant discarded and the pellet again suspended in PBS. An aliquot of these liposomes is then taken and mixed with scintillation fluid to determine the radioactivity of the $^{32}$P-end labelled oligodeoxynucleotide thus encapsulated in liposomes. The initial oligodeoxynucleotide input concentration appears to determine the encapsulation efficiency of the oligodeoxynucleotide.

For example, with an oligodeoxynucleotide concentration of 0.1 ug input dose, the percent encapsulation in liposomes ranges from 65 to 90%. With an initial oligodeoxynucleotide concentration of 35 and 50 ug, however, the percent encapsulation varies from 58 to 50% and a further decrease in encapsulation is obtained if the oligodeoxynucleotide concentration is raised to 100 ug. The total concentration of oligodeoxynucleotide available encapsulated in liposomes, however, is substantially high ranging from 45 to 65% of the initial input dose.

Having described the present invention, the same will now be further illustrated by reference to the following examples which are provided solely for purposes of illustration and are not intended to be limitative.

EXAMPLE 1

Encapsulation by the Minimal Volume Technique

Phosphatidylcholine, cardiolipin and cholesterol were added together at a molar ratio of 10:2:6.8 and mixed thoroughly and dried by evaporation under vacuum. To this lipid mixture 10 µl of PBS containing oligodeoxynucleotides was added for each 4.5 mg of lipids. The whole mixture was left overnight at 4° C. for incubation following which 40 µl of additional PBS was added to the hydrated film and vortexed vigorously. The mixture was further hydrated for one hour at 4° C. followed by addition of 250 µl of PBS. The liposomes were then sonicated for 3 minutes at 90% output with a W370 heat system cup horn sonicator. The liposomes were then left at 4° C. for additional 30 minutes. The unentrapped oligodeoxynucleotides were separated by centrifugation at 18,000 rpm for 10 minutes. The pellet was refreshed with PBS, centrifuged again at 18,000 rpm, the supernatant was discarded and the pellet was again suspended in PBS.

An aliquot of these liposomes were taken and mixed with scintillation fluid to determine the radioactivity of the $^{32}$P-end label oligodeoxynucleotide thus encapsulated. It is noted that the encapsulation efficiency obtained is generally sufficient to perform any in vitro and in vivo study with the oligodeoxynucleotides.

EXAMPLE 2

In Vitro Stability of Liposomally Encapsulated Oligodeoxynucleotides

The oligodeoxynucleotides were encapsulated in liposomes as described above and the amount of oligodeoxynucleotide present in the liposomes was determined by counting the radioactivity as described. The liposomes were then left at 4° C. for 1 week. After this period, the liposomes were centrifuged and the supernatant was discarded. The pellet was resuspended in a known value of PBS and an aliquot was taken to measure the radioactivity, to determine the total amount of oligodeoxynucleotide present in the liposomes. It was determined that storing liposomes at 4° C. for one week affects only 14% loss of the oligodeoxynucleotide and 85% remained encapsulated in the liposomes. This clearly demonstrates that the present liposomally encapsulated oligonucleotides are quite stable and capable of long-term storage.

EXAMPLE 3

Effect of Nuclease Activity on Oligonucleotide Encapsulate in Liposomes

In order to demonstrate that the encapsulated oligonucleotides are inside of the liposomes, as opposed to being attached to the liposome surface, the oligodeoxynucleotide-liposomes were digested with nucleases. Lipsomally encapsulated oligodeoxynucleotides were incubated for 30 minutes and 37° C. in the presence of an excess of micrococcal nuclease in 1 mM $CaCl_2$.

After this period of incubation, the liposomal oligodeoxynucleotides were centrifuged at 18,000 rpm for 10 minutes, the supernatant discarded, the pellet washed twice with PBS and centrifuged again. The final pellet was suspended in PBS and an aliquot of liposomes was mixed with scintillation fluid for radioactivity measurement to determine the concentration of the oligonucleotides and liposomes. The liposomes thus digested with nucleases showed 91% of the radioactivity inside the liposomes compared to the original liposomes. This experiment showed that only 9% of the oligodeoxynucleotides were attached to the surfaces of the liposome and 91% of the oligodeoxynucleotides were inside the liposomes and fully protected from nuclease attack.

EXAMPLE 4

Cellular Accumulation of Liposomally Encapsulated Oligodeoxynucleotides

The $^{32}$P-end labeled oligodeoxynucleotides (dT15) were encapsulated in liposomes and were used to determine the cellular uptake in A549 and SQ-20B human cancer cells in comparison to free oligonucleotides. Logarithmically growing A549 and SQ-20B cells ($5 \times 10^5$ cells/well, in 6 well culture plates) were treated with labeled free oligo(dT15) and liposomal oligo at 37° C. for 4 hr. After incubation, the cells were washed 3 times with PBS, trypsinized and centrifuged in 25 ml of 0.2M glycine (pH 2.8). The pellet was finally suspended in 1 ml of 1N NaOH and incubated overnight at 65° C. The amount of cell associated radioactivity was determined by scintillation counting from the cell homogenate.

Figure 2:
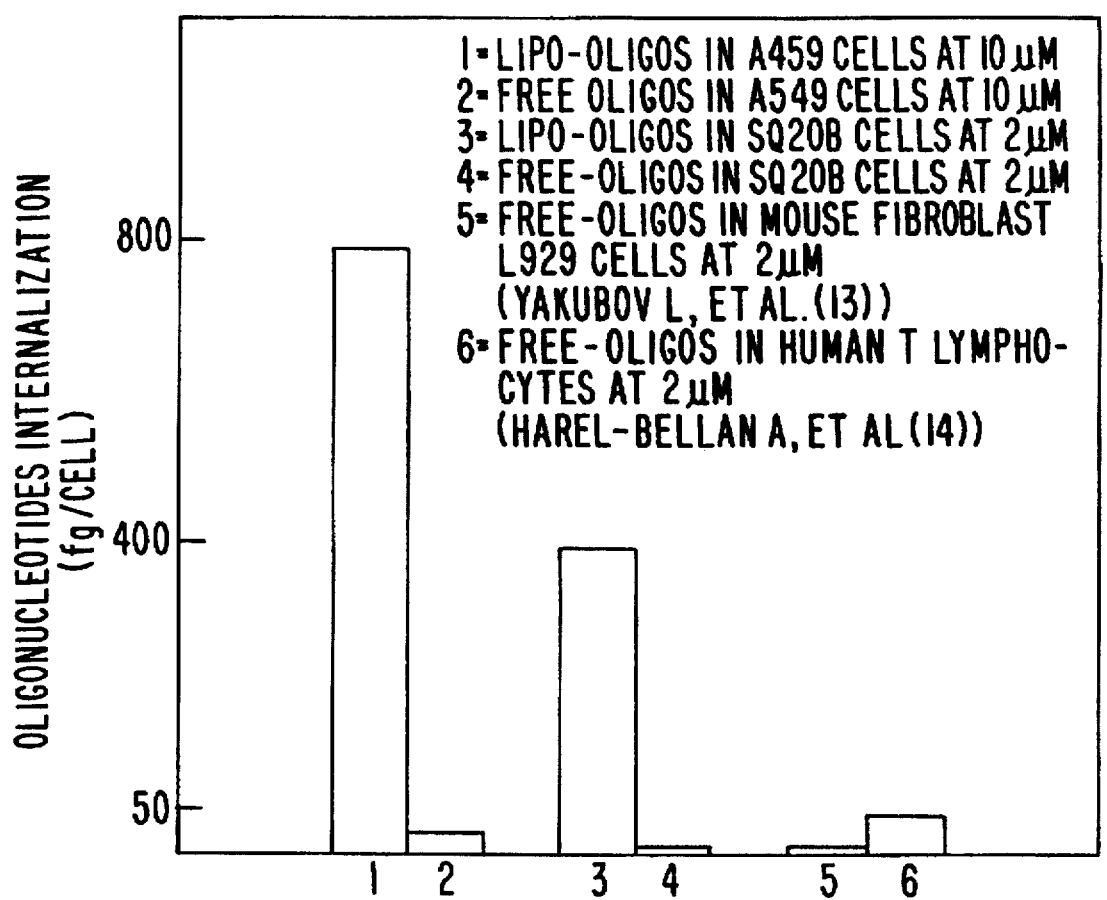
FIG. 2 illustrates the cellular uptake of free and liposomal encapsulated oligodeoxynucleotides.

The maximum cellular uptake of liposomal oligodeoxynucleotide was obtained in 3 hr and then plateaued either with A549 or SQ-20B cells. With A549 cell exposure to liposomal oligos at a concentration of 10.0 μM for 4 hr produced a maximal oligo concentration of 800 fg/cell. However, free oligo at a concentration of 10 μM for 4 hr produced only 31 fg/cell oligo uptake. Hence at equivalent levels of liposomal encapsulated and free oligodeoxynucleotides, the cell associated oligos were 25–30 fold higher with liposomal delivery than the free oligodeoxynucleotides as shown in FIG. 2. The same temporal relationship was observed in SQ-20B cells. The SQ-20B cells when exposed with 2 μM of liposomal oligodeoxynucleotide produced 396 fg/cell whereas free oligodeoxynucleotide at the same concentration of exposure provided 12 fg/cell associated nucleotide. Hence, these experiments demonstrate that liposomally encapsulated oligodeoxynucleotides are internalized into the cells 30–40 fold higher than free oligodeoxynucleotide. This is a major advantage in relation to biological activity of these potential therapeutic agents. FIG. 2 also shows the values reported in the literature of cellular uptake of free oligodeoxynucleotides. Our data is in agreement with previous observations in relation to the entry of free oligonucleotides.

Figure 3:
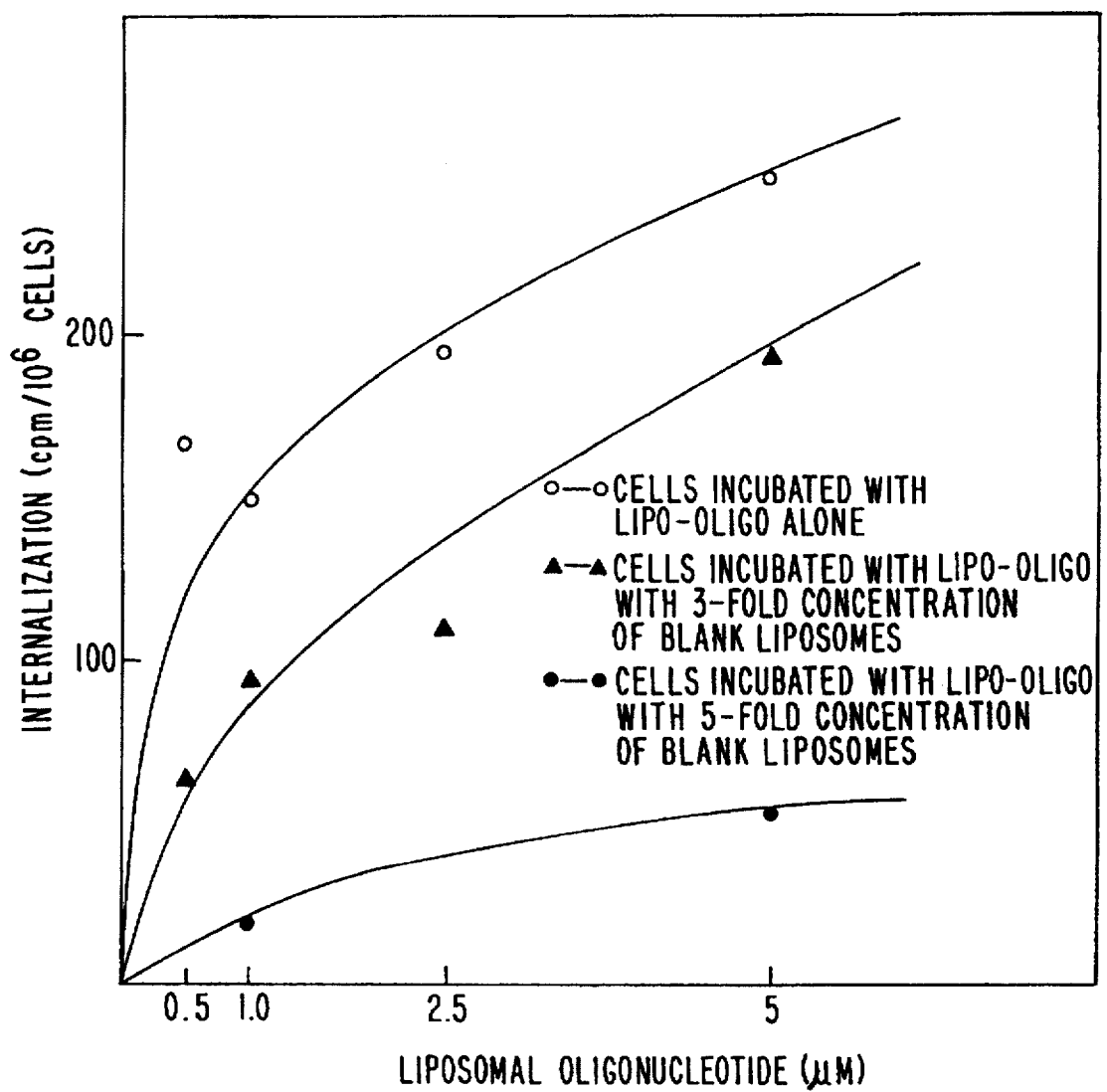
FIG. 3 illustrates the inhibition of internalization of liposomal oligodeoxynucleotides by blank liposomes.

A series of experiments were performed to confirm the specific uptake by liposomally encapsulated oligodeoxynucleotides into human cancer cells. The human cancer cells were exposed to liposomal oligodeoxynucleotides concurrently with the blank liposomes having 3-fold higher lipid concentration than the liposomes with the encapsulated oligodeoxynucleotides (FIG. 3). In this experiment, 20% inhibition of oligodeoxynucleotide uptake in human cancer cells was observed. In other experiments, where 5-fold higher blank liposomes were utilized concurrently with liposomal oligodeoxynucleotides for incubation to cancer cells, 64% inhibition of oligodeoxynucleotide uptake in cells was observed. These experiments demonstrated (1) that there is specific cellular uptake of liposomal oligodeoxynucleotideds, (2) the uptake is inhibited by blank liposomes and is dependent on the lipid concentration, (3) blank liposomes may saturate the cell surfaces and hence liposomal oligodeoxynucleotides cannot penetrate the cell membranes in such situations. On the other hand, the endocytosis of cells appears to play an important role and blank liposomes do saturate that process resulting in reduced internalization of the liposomal oligos. This is further supported by our following experiments.

EXAMPLE 5

Determination of the Effect of NaN$_3$ on Liposomal Oligodeoxynucleotide Internalization Sodium azide (NaN$_3$) is a known inhibitor of endocytosis in cells. To determine whether liposomal oligodeoxynucleotides are internalized by endocytosis in cells, they were treated with NaN$_3$. SQ-20B human head and neck cancer cells were preincubated in the presence of 10 mM NaN$_3$ for 2 hr at 37° C. Following this period of incubation, the cells were exposed to $^{32}$P-end labeled oligodeoxynucleotides encapsulated in liposomes for 4 hr at 37° C. in the medium containing NaN$_3$. The cells were than harvested, pelleted and washed in 0.2M glycine (pH 2.8) and the intracellular radioactivity was determined. The intracellular accumulation of liposomal oligodeoxynucleotides was inhibited 79% as compared to the cells which were exposed with the same concentration of liposomal oligodeoxynucleotides without NaN$_3$ treatment. Hence, it appears that the major route of cellular uptake for liposomal oligodeoxynucleotides is endocytosis.

EXAMPLE 6

Stability of Oligodeoxynucleotides Encapsulated in Liposomes in the Medium

To determine the stability of oligodeoxynucleotides in the medium, the oligodeoxynucleotides were exposed both in free and in liposome encapsulated form from 30 min to 1 week at 37° C. An aliquot of the sample from the medium was taken and gel electrophoresis with 20% polyacrylamide was performed essentially according to the method of Laemmli. Nature 227, 680–685 (1970). In addition, liposomes with encapsulated oligodeoxynucleotides which were stored at 4° C. for a stability determination were also utilized for gel electrophoresis to confirm their integrity. After electrophoresis, the gel was subjected to x-ray film (X-Omat, AR2, Kodak) for autoradiography. The free oligodeoxynucleotides were mostly degraded within half an hour after exposure in the medium since only a very slight band was observed. By 4 hr, all the free oligodeoxynucleotides were degraded and no band was observed. However, oligodeoxynucleotides encapsulated in liposomes showed a very significant stability when exposed to the medium. The bands of the oligodeoxynucleotides encapsulated in liposomes were present in the same intensity until 1 week as compared to the control bands. In addition, liposomal oligodeoxynucleotides which were stored at 4° C. showed similar intensity in bands confirming their stability at storage. Hence, these experiments demonstrate that a major impediment to oligodeoxynucleotide stability in a biological environment can effectively be overcome by encapsulating the oligodeoxynucelotides in liposomes.

EXAMPLE 7

Determination of Stability of Liposomal Oligodeoxynucleotides in the Human Cancer Cells Liposomally encapsulated [$^{32}$P]-oligodeoxynucleotides were incubated with A549 human lung cancer cells as described previously. Following incubation, the drug containing medium was removed and saved. The cells were rinsed 3 times with PBS, trypsinized and counted. The cells were then centrifuged for 5 min at 1000 g. The resulting cell pellet was lysed in 0.1 ml Tris-buffered saline (10 mM, Tris-HCl, pH 7.4 with 150 mM NaCl) with 1% sodium dodecylsulfate and then extracted with 0.1 ml of phenol. The aqueous phases were combined and to determine the stability of oligodeoxynucleotides, the extracts were lyophilized and redissolved in 50 µl of 1% SDS containing 20% (vol/vol) glycerol following which gel electrophoresis with 20% polyacrylamide was performed essentially according to the method of Laemmli. After electrophoresis, the gel was subjected to x-ray film (X-Omat, AR, Kodak) for autoradiography.

The autoradiograph demonstrated that the intact oligodeoxynucleotides were present as shown by the persistence of bands after 4 hr of liposomal oligodeoxynucleotides incubation in the cells. However, by 24 hr after the initial of 4 hr incubation of cells with liposomally encapsulated oligodeoxynucleotides, no bands were observed. This is apparently due to the fact that liposomal oligodeoxynucleotides inside the cells are acted upon by the enzymes and thus are being degraded. However, the cellular stability of the liposomal oligodeoxynucleotides appears to be sufficient to result in the desired biological effect.

EXAMPLE 8

Cytotoxicity Evaluation of Antisense Oligodeoxynucleotides Both as Free or Encapsulated in Liposomes Antisense oligodeoxynucleotides designed to hybridize with the 5'-end of the reported sequence for the human poly(ADP-ribose) polymerase were synthesized. In this preliminary experiment, the phosphorothionate derivative of the antisense sequence was used to evaluate the cell growth of human lung cancer A549 cells. With these cells, a clonogenic assay was performed to evaluate the toxicity of the S-substituted oligodeoxynucleotide in the free or liposomal form. Briefly, an accurately known number of cells were plated in a 10 cm² culture well and after overnight incubation were treated at different concentrations of the free oligodeoxynucleotides or liposomal oligodeoxynucleotides for 15 hr at 37° C. Following the antisense exposure, the cells were washed twice with PBS and fresh medium was added. The cells were left in the incubation for 15 days to develop colonies. The resulting colonies were then stained with methylene blue and counted. Percent survival of treated cells was determined relative to untreated control.

The A549 cells treated with free oligodeoxynucleotides showed only 30% cytotoxity compared to the controls even at exposure concentrations of 2.0 µM. However, liposomal oligodeoxynucleotides at exposure concentration of 0.2 µM demonstrated 90% cytotoxicity to these human lung cancer cells. The magnitude of difference in cytotoxicity is the result of using specific antisense oligodeoxynucleotides when delivered in liposomes to inhibit the poly(ADP-ribose) polymerase in the cells. These experiments evidence that antisense oligodeoxynucleotides complementary to the gene effectively reduce transcription and regular RNA synthesis leading to the eventual death of the cells. We expect that the same sensitization of A549 lung cancer cells to radiation and drugs after incubation with liposomal oligodeoxynucleotides.

The present invention also provides pharmaceutical compositions containing the present liposomes. These compositions are used to treat malignant cells, or viruses or both and may contain any number of different pharmaceutical adjuvants such as other cancer chemotherapeutic agents or anti-viral agents. The compositions may contain, generally, from 0.1 to 99.9% by weight of the present liposomes.

For example, the present liposome encapsulated oligonucleotide may be mixed with any anti-viral agent such as, for example, azidothymidine or any of the sulfated polysaccharides such as dextran sulfate. The encapsulated oligonucleotides may even be intermixed with anticancer agents such as vincristine, vinblastine or methotrexate. Of course, the encapsulated oligonucleotides may be intermixed with pharmaceutically inert diluents or carriers.

Additionally, in accordance with the present invention, various oligodeoxynucleotides may be encapsulated in order to inhibit gene expression. The following listing includes a non-exhaustive, illustrative listing of target gene examples for a variety of uses:

inhibition of viral gene expression inhibition of oncogene expression inhibition of genes coding for proteins which are involved in the manifestation of a disease or phenotype.

Examples of viral genes which can be modulated using liposomal oligodeoxynucleotides:

human immunodeficiency virus (HIV)

herpes simplex virus (HSV)

vesicular stomatitis virus lymphotropic virus

Epstein Barr virus (EBV)

rous sarcoma virus (RSV)

Simian virus 40 (SV40)

Encephalo-myocarditis virus (EMCS)

Examples of oncogenes which can be modulated using liposomal oligonucleotides:

raf c myc c-fos ras c-myb

Examples of genes coding for proteins which are involved in the manifestation of a disease or a phenotype and which expression can be regulated using liposomal oligonucleotides:

dihydrofolate reductase gene poly(ADP-ribose) polymerase gene multidrug resistance genes HLA proteins genes receptor protein genes gene of antibodies protecting against a viral or bacterial disease.

In accordance with the present invention, analogs of oligonucleotides may also be encapsulated. The term "analog" is used to refer to any chemically modified oligonucleotide sequence. For example, oligonucleotide analogs can be synthesized which have increased resistance to nuclease cleavage. For example, methylphosphonate, phosphorothioate and phosphoramidate oligonucleotide analogs can be prepared in accordance with well known procedures.

At present, many gene sequences are known which would be susceptible to translation or transcription arrest in accordance with the present invention. For example, the following gene sequences are described in the publications cited: HIV, Wain-Hobson S., et al: *Cell* 40:9–17 (1985); c-myb; Westin E. W. et al: *Proc. Natl. Acad. Sci. USA* 79:2194 (1982); HSV; Watson R. J.: *Nucleic Acids Res.* 10:979–991 (1982); VSV, Emerson M. J. et al: *J. Biol. Chem.* 260:9085–9087 (1985); c myc, Watt R. et al: *Nature* 303:725–728 (1983); raf, Okayama H et al: *Mol. Cell. Biol.* 3:280 (1983); poly ADP-ribose polymerase, Cherney B. W. et al: *Proc. Natl. Acad. Sci. USA* 84:8370–8374 (1987) and mdr genes, Chen C. J. et al: *Cell* 47:381–389 (1986). These are provided solely for illustration and are not intended to be limitative.

Upon selecting a particular target gene of interest, the following general methodology may be used to guide the artisan in designing a suitable antisense oligonucleotide capable of inhibiting the expression of that gene.

First, translated DNA sequences and mRNA sequences from a given gene may be determined, if not already known, by well known DNA sequencing methods. For example, see Current Protocols in Molecular Biology (Wiley, 1987) for chapters relating to the preparation and analysis of DNA and RNA. DNA sequencing and the construction and screening of DNA libraries. A suitable antisense oligonucleotide sequence is designed to be complimentary to a sequence of DNA or mRNA and having the general length as described above.

Second, the specificity of the antisense oligonucleotide will depend upon its length. Generally, it has been assumed throughout the molecular biology community that no 12-base sequence will appear more than once in the human genome. Hence, efficacy can be obtained with as few as 4 mer or up to about 15 mer. Most preferably, oligonucleotide sequences of from 4 to 13 mer are used.

Third, when an RNA is targeted the antisense oligonucleotide must be designed to bind to a homologous sequence located in a single-stranded region of an RNA. Thus, it is preferable to know the secondary structure of an RNA.

Fourth, in order to completely inhibit protein synthesis, it is preferred to target sequences from the translation initiation region or transcription initiation region of the targeted gene sequence.

As noted above, the present invention provides a method of encapsulating oligonucleotides by minimal volume entrapment. This method enables the formation of a significant percentage of liposomally encapsulated oligonucleotides which are then readily isolable. In this method, after adding the oligonucleotide portion to the dried lipid mixture, and incubating the mixture, the incubated mixture is further mixed. This further mixing appears to increase the volume of the formed liposomes, preventing the formation of gel. The liposomally entrapped oligodeoxynucleotides can then be removed by centrifugation or even dialysis.

As a preferred method, however, it is desirable to sonicate the liposomes after mixing the incubated mixture and prior to removing the entrapped oligodeoxynucleotides. It appears that the sonication has the effect of reducing the liposome size making them more effective for therapeutic use.

Additionally, it is noted that the term "substantially hybridizable" generally means a degree of complementarity of at least about 50% of the oligonucleotide for the target gene sequence. It is preferred, however, that the degree of complementarity be at least about 75%, and even more preferably in excess of 90%. Thus, the most preferred oligonucleotide sequences used in accordance with the present invention are those which have at least about 75%, and preferably in excess of 90%. Thus, the most preferred oligonucleotide sequences used in accordance with the present invention are those which have at least about 75%, and preferably in excess of 90% complementarity with the translation or transcription invitation region of the targeted gene sequence, and which also have a length of about 4 to 20 mer.

Having described the present invention, it will be apparent to one of skill in the art that many modifications and changes can be made to the above described embodiments while remaining within the spirit and the scope of the present invention.

What is claimed as new and desired to be secured by Letters Patent of the United States is:

1. A method of encapsulating an oligodeoxynucleotide or an analog thereof in liposomes, which comprises:
    a) mixing lipids for constituting said liposomes, and drying said lipids under reduced pressure;
    b) adding to said dried lipids a solution comprising said oligodeoxynucleotide or said analog thereof, wherein said analog is a methylphosphonate, phosphorothioate or phosphoramidate analog, at a ratio of about 1–3 μl of oligonucleotide-containing solution per mg of lipid,
    c) incubating said lipids and said solution for about 4 to 24 hours, and then mixing said lipids and said solution, whereby liposomes are formed; and
    d) separating said liposomes from oligodeoxynucleotide or oligodeoxynucleotide analog that is not encapsulated in said liposomes, such that said method incorporates at least about 45% of said oligodeoxynucleotide or said analog thereof into said isolated liposomes.

2. The method of claim 1, which further comprises, after step c) and before step d) sonicating said liposomes.

3. The method of claim 1, wherein said liposomes are separated from oligodeoxynucleotide or oligodeoxynucleotide analog that is not encapsulated in said liposomes by centrifugation or dialysis.

* * * * *